United States Patent
Ben Chaabane et al.

(10) Patent No.: US 11,560,581 B2
(45) Date of Patent: Jan. 24, 2023

(54) PROCESS FOR PRODUCING ENZYMES WITH A STRAIN BELONGING TO A FILAMENTOUS FUNGUS

(71) Applicant: IFP Energies nouvelles, Rueil-Malmaison (FR)

(72) Inventors: Mohamed Fadhel Ben Chaabane, Rueil-Malmaison (FR); Etienne Jourdier, Rueil-Malmaison (FR); Caroline Aymard, Rueil-Malmaison (FR); Frederic Augier, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/950,428

(22) Filed: Nov. 17, 2020

(65) Prior Publication Data
US 2021/0147893 A1  May 20, 2021

(51) Int. Cl.
  *C12N 9/24* (2006.01)
  *C12P 19/14* (2006.01)
  *C12P 21/00* (2006.01)

(52) U.S. Cl.
  CPC ............ *C12P 21/00* (2013.01); *C12N 9/2402* (2013.01); *C12P 19/14* (2013.01); *C12Y 302/01004* (2013.01)

(58) Field of Classification Search
  CPC .................. C12N 9/2402; C12P 19/14; C12Y 302/01004
  See application file for complete search history.

(56) References Cited

U.S. PATENT DOCUMENTS

| | | | |
|---|---|---|---|
| 8,956,846 B2 | 2/2015 | Ben Chaabane et al. | |
| 8,993,294 B2 | 3/2015 | Bodo et al. | |
| 10,822,600 B2 * | 11/2020 | Ben Chaabane | C12P 21/00 |
| 2011/0081697 A1 * | 4/2011 | Liu | C12P 7/10 |
| | | | 435/162 |
| 2012/0220009 A1 * | 8/2012 | Bodo | B01D 61/22 |
| | | | 530/418 |
| 2012/0252066 A1 | 10/2012 | Heng et al. | |
| 2014/0302587 A1 * | 10/2014 | Ben Chaabane | C12N 9/2437 |
| | | | 435/209 |
| 2015/0057434 A1 | 2/2015 | Schelle | |
| 2019/0085310 A1 | 3/2019 | Ben Chaabane et al. | |

FOREIGN PATENT DOCUMENTS

| | | |
|---|---|---|
| DE | 102010063942 A1 | 6/2012 |
| EP | 2371950 B1 | 9/2013 |
| WO | 11019686 A1 | 2/2011 |
| WO | 12142557 A1 | 10/2012 |
| WO | 13026964 A1 | 2/2013 |
| WO | 17174378 A1 | 10/2017 |

OTHER PUBLICATIONS

Serrano-Carreon et al., Adv Biochem Eng Biotechnol (2015) 149: 55-90).*
Search report in corresponding FR 1912856 dated Jul. 6, 2020 (pp. 1-5).

* cited by examiner

*Primary Examiner* — Maryam Monshipouri
(74) *Attorney, Agent, or Firm* — Millen, White, Zelano & Branigan, PC; Ryan Pool

(57) ABSTRACT

A process for producing cellulolytic and/or hemicellulolytic enzymes with a strain of microorganism belonging to the family of filamentous fungi. The process includes growing the fungi in an aqueous culture medium, in the presence of at least one carbon-based growth substrate, in a stirred and aerated bioreactor. It also includes the production of enzymes, starting with the aqueous culture medium in the presence of at least one inductive carbon-based substrate and also inducing the production of hydrophobins. Further, at least a portion of the hydrophobins produced in step (b) are reintroduced into the growth step (a).

16 Claims, 1 Drawing Sheet

PROCESS FOR PRODUCING ENZYMES WITH A STRAIN BELONGING TO A FILAMENTOUS FUNGUS

TECHNICAL FIELD

The invention relates to a process for producing cellulases with a filamentous fungus, required for the enzymatic hydrolysis of lignocellulosic biomass used, for example, in processes for producing "second generation" (2G) sugary liquors. These sugary liquors may be used to produce other products via a chemical or biochemical/fermentation pathway (for example alcohols such as ethanol biofuels, or else butanol or other molecules, for example solvents such as acetone and other biobased molecules, etc.). Cellulases may also be used in other processes, notably in the chemical, paper or textile industry.

The development of economically viable processes for producing second-generation (2G) biofuels, to take this particular example of implementation, is the subject of numerous studies. These biofuels are notably produced from ligneous substrates such as various woods (hardwood and softwood, miscanthus, or SRC, which is the abbreviation for Short-Rotation Coppice), agricultural byproducts (wheat straw, rice straw, corn cobs, etc.) or byproducts from other agrifood, paper, etc. industries. They pose fewer problems of competition with subsistence crops for the use of agricultural land, when compared with "first-generation" biofuels which are produced from sugarcane, corn, wheat or beet.

Lignocellulosic biomass is characterized by a complex structure composed of three main fractions: cellulose (35% to 50%), which is a polysaccharide essentially constituted of hexoses; hemicellulose (20% to 30%), which is a polysaccharide essentially constituted of pentoses; and lignin (15% to 25%), which is a polymer of complex structure and of high molecular weight, composed of aromatic alcohols connected via ether bonds. These various molecules are responsible for the intrinsic properties of the plant wall and organize themselves into a complex entanglement. Among the three base polymers that make up the lignocellulosic biomass, cellulose and hemicellulose are the ones that enable the production of 2G sugary liquors.

Conventionally, the process for transforming biomass into ethanol biofuel involves several steps: Pretreatment makes the cellulose accessible to the cellulase enzymes. The enzymatic hydrolysis step allows the transformation of cellulose into sugars, such as glucose, which are then transformed into ethanol during the fermentation step, generally with the yeast *Saccharomyces cerevisiae*. Finally, the distillation step makes it possible to separate and recover the ethanol from the fermentation must.

It should be noted, as mentioned above, that it may also be chosen to stop the process at the production of monomer sugars such as glucose, xylose, etc. in order to upgrade them as such, or else to process them differently in order to obtain other biobased alcohols or molecules.

PRIOR ART

Various technico-economic studies demonstrate that reducing the cost of cellulases is one of the key points in processes for the biological production of ethanol from lignocellulosic raw materials. At the present time, industrial cellulases are mainly produced by a filamentous fungus, *Trichoderma reesei*, on account of its high secretory power.

Since the 1970s, the transformation of lignocellulosic materials into ethanol, after hydrolysis of the constituent polysaccharides into fermentable sugars, has been the subject of numerous studies. Mention may be made, for example, of the reference studies by the National Renewable Energy Laboratory (Process Design and Economics for Biochemical Conversion of Lignocellulosic Biomass to Ethanol, Humbird et al., NREL/TP-5100-57764, May 2011).

Lignocellulosic materials are cellulose-based materials, i.e. materials consisting to more than 90% by weight of cellulose, and/or are lignocellulosic materials, i.e. materials consisting of cellulose, hemicelluloses, which are polysaccharides essentially consisting of pentoses and hexoses, and also lignin, which is a macromolecule of complex structure and of high molecular weight, based on phenolic compounds.

Wood, straw and corn cobs are the lignocellulosic materials most commonly used, but other resources, dedicated forestry crops, residues from alcohol-yielding, sugar-yielding and cereal plants, products and residues from the paper industry and products from the transformation of lignocellulosic materials are usable. They are for the majority constituted of about 35% to 50% of cellulose, 20% to 30% of hemicellulose and 15% to 25% of lignin.

The process for the biochemical transformation of lignocellulosic materials into ethanol comprises a physicochemical pre-treatment step, followed by a step of enzymatic hydrolysis using an enzyme cocktail, a step of ethanolic fermentation of the sugars released, the ethanolic fermentation and the enzymatic hydrolysis possibly being conducted simultaneously, and a step of purification of the ethanol.

The enzyme cocktail used for the enzymatic hydrolysis is a mixture of cellulolytic enzymes (also known as cellulases) and/or hemicellulolytic enzymes. Cellulolytic enzymes have three major types of activities: endoglucanases, exoglucanases and cellobiases, the latter also being known as β-glucosidases. Hemicellulolytic enzymes notably have xylanase activities.

Enzymatic hydrolysis is efficient and is performed under mild conditions. However, the cost of the enzymes remains very high, representing from 20% to 50% of the cost of transformation of lignocellulosic material into ethanol. As a result, numerous studies have been conducted to reduce this cost: first, optimization of the production of enzymes, by selecting hyper-productive microorganisms and by improving the processes for producing said enzymes, reduction of the amount of enzymes subsequently in hydrolysis, by optimizing the pretreatment step, by improving the specific activity of these enzymes, and by optimizing the implementation of the enzymatic hydrolysis step.

Numerous studies have focused on understanding the mechanisms of action and expression of the enzyme cocktail. The aim is to secrete the cocktail that is the most suitable for the hydrolysis of the lignocellulosic materials by modifying the microorganisms.

*Trichoderma reesei* is the microorganism most widely used for the production of cellulases. The wild-type strains have the faculty of excreting, in the presence of an inductive substrate, for example cellulose, the enzymatic complex considered as being the best suited for the hydrolysis of cellulose. The enzymes of the enzymatic complex contain three main types of activities: endoglucanases, exoglucanases and cellobiases and other proteins which have properties that are essential for the hydrolysis of lignocellulosic materials are also produced by *Trichoderma reesei*, for example xylanases. The presence of an inductive substrate is essential for the expression of the cellulolytic and/or hemicellulolytic enzymes. The nature of the carbon-based substrate has a strong influence on the composition of the enzymatic complex. This is the case for xyloses, which, when combined with a carbon-based inductive substrate such as cellulose or lactose, make it possible to significantly improve the activity of said xylanase. Regulation of the cellulase genes on various carbon sources has been studied in detail. They are induced in the presence of cellulose, of its hydrolysis products, such as cellobiose, or of certain oligosaccharides such as lactose or sophorose (cf. Ilmén et al., 1997; Appl. Environ. Microbiol. 63. 1298/1306).

Conventional genetic mutation techniques have enabled the selection of strains of *Trichoderma reesei* which hyperproduce cellulases, such as the strains MCG77 (Gallo—U.S. Pat. No. 4,275,167), MCG 80 (Allen, A. L. and Andreotti, R. E., Biotechnol.-Bioeng. 1982, 12, 451-459 1982), RUT C30 (Montenecourt, B. S. and Eveleigh, D. E., Appl. Environ. Microbiol. 1977, 34, 777-782) and CL847 (Durand et al., 1984, Proc. Colloque SFM "Gënëtique des microorganismes industriels [Genetics of industrial microorganisms]". Paris. H. Heslot Ed, pages 39-50).

The process for producing cellulases by *Trichoderma reesei* has been the subject of substantial improvements for the purpose of extrapolation to the industrial scale. To obtain good enzyme productivities, it is necessary to supply a source of rapidly assimilable carbon for the growth of *Trichoderma reesei* and an inductive substrate which allows the expression of the cellulases and secretion into the culture medium. Cellulose can play these two roles; however, it is difficult to use at the industrial stage and it has been proposed to replace it with soluble carbon sources, such as glucose, xylose or lactose, lactose also acting as inductive substrate. Other soluble sugars such as cellobiose and sophorose have been described as inductive, but they are relatively expensive for use at the industrial stage. It has also been found that productions of cellulases by *Trichoderma reesei*, with soluble substrates, are very much inferior to those obtained on cellulose by "batch". This is due to the repressor effect of the readily assimilable sugars, at high concentration. Continuous feeding in fed-batch mode of soluble carbon-based substrates has made it possible to raise the catabolic repression by limiting the residual concentration in the cultures and by optimizing the amount of sugar, making it possible to obtain a better yield and better enzymatic productivity.

Patent FR-B-2 555 603 proposes a protocol for arriving at a protein concentration of the order of 35 to 40 g/L with a productivity of the order of 0.2 g/L/h and which consists of two steps: a first step of growth in "batch" mode in which it is necessary to supply a source of rapidly assimilable carbon for the growth of *Trichoderma reesei*, and then a step of production in "fed-batch" mode using an inductive substrate (for example: lactose) which allows the expression of the cellulases and secretion into the culture medium. The optimum flow applied is between 35 and 45 mg·g-1·h-1 (milligrams of inductive substrate per milligram of biomass and per hour). Mention may also be made of patent EP-B-2 744 899 which proposes an improvement thereto, by notably selecting a bioreactor which has a particular coefficient of volumetric transfer of oxygen kLa, combined with a particular selection both of the concentration of carbon-based growth substrate in the first step and of a level of flow limiting the source of carbon in the second step.

Moreover, the filamentous fungus *Trichoderma reesei* is known for its strict aerobic nature: it has poor tolerance to a lack of dissolved oxygen. It is possible to define a minimum concentration of dissolved oxygen permitting satisfactory culturing, this concentration generally being between 1 and 5 mg/L.

As detailed in the 2012 article by Gabelle J.-C., Jourdier E., Licht R. B., Ben Chaabane F., Henaut I., Morchain J., and Augier F. "Impact of rheology on the mass transfer coefficient during the growth phase of *Trichoderma reesei* in stirred bioreactors" (Chemical Engineering Science 75 (2012) 408-417), to perform culturing under good oxygenation conditions, the reactor used (also known as the fermenter) is generally designed and operated so as to be able to perform an oxygen transfer sufficient to achieve the minimum concentration of dissolved oxygen mentioned above throughout the culturing. Now, throughout the enzyme production process, comprising the step of growth of the fungi and then the step of enzyme production per se, the most intricate part for respecting this criterion of minimum concentration of dissolved oxygen proved to be the end of the growth step, since this is both the moment when the oxygen demand is greatest, and the moment when the viscosity of the fermentation must tends to be the highest.

Now, it is known that the viscosity has a negative impact on the oxygen transfer (Gabelle et al., 2011—Gabelle J. C., Jourdier E., Licht R. B., Ben Chaabane F., Henaut I., Morchain J. and Augier F. (2012) Impact of rheology on the mass transfer coefficient during the growth phase of *Trichoderma reesei* in stirred bioreactors. Chemical Engineering Science 75, 408-417): the more the biomass concentration increases, the more the flow of oxygen to be transferred tends to increase, but the more difficult this transfer is to achieve due to this increase in viscosity, which may make it necessary to adapt the operating conditions. The flow of oxygen transferred from a gas phase to a liquid is conditioned by numerous parameters, such as the partial pressure of oxygen in the gas phase, the pressure in the reactor, the flow rate of injected air, the concentration of dissolved oxygen and the power dissipated by mechanical stirring, if any, in the fermenter.

Generally, the gas injected is air, for economic reasons. Furthermore, the pressure can only be increased by a few bar since, beyond this, the concentration of dissolved $CO_2$ may inhibit the culture. These two action levers have a direct impact on the enzyme production viability, since they potentially increase the energy consumption, or even the investments, for the facilities performing this process.

In a given fermenter, having well known maximum aeration and stirring capacities, it is not envisageable to exceed a certain concentration of biomass at the end of growth. The reason for this is that, once the aeration and stirring have been pushed to their maximum level, once the required minimum concentration of dissolved oxygen has been reached, any increase in the concentration of biomass would induce both an increase in the oxygen demand and an increase in the viscosity, leading to a decrease in the concentration of dissolved oxygen, which may harm the overall fermentation yield. It is thus seen that the need for this transfer of oxygen to the liquid phase in the fermenter creates industrial/economic constraints which have an impact on the overall yield of enzyme production.

It is moreover known practice from patent application EP-1 204 738 to genetically modify fungal strains, notably of *Trichoderma* type, and most particularly the DNA sequences thereof coding for hydrophobins, in order to prevent the strains from secreting these hydrophobins, and notably HFBIIs, which are considered to be responsible for the formation of foam. However, any solution involving genetic modifications is laborious to implement, since it requires that these genetic modifications be performed on each of the strains of interest.

The aim of the invention is thus an improved process for producing enzymes, which is notably directed towards overcoming the abovementioned drawbacks. The aim of the invention is notably to improve the productivity of the process, notably by improving/increasing the transfer of oxygen into the liquid phase of the reactor using it without adding/while limiting any additional constraint on the operating conditions or the design of the reactor.

The subject of the invention is firstly a process for producing cellulolytic and/or hemicellulolytic enzymes with a strain of microorganism belonging to the family of filamentous fungi, such that said process comprises (for example consists of) the following steps:

(a) a first step of growing the fungi in an aqueous culture medium, in the presence of at least one carbon-based growth substrate, in a stirred and aerated bioreactor, notably in batch phase, (b) a second step of producing enzymes, starting with the aqueous culture medium obtained in the first step (a), in the presence of at least one inductive carbon-based substrate, also inducing the production of hydrophobins, and in which, in a step (d), at least a portion of the hydrophobins produced in step (b) are reintroduced into the growth step (a).

The inventors in fact studied the transfer of oxygen between a liquid phase (the culture medium) and a gas phase (oxygen, or more generally air) supplying the oxygen required by the fungi to grow and to produce the desired enzymes, this transfer involving many physical parameters. It turned out that a magnitude of great importance on the oxygen transfer is the size of the bubbles. Specifically, the smaller the bubbles, the more exchange surface the injected air will generate. It is in fact mainly for this reason that a stirring device is often used in fermenters, to reduce the bubble size and thus to increase the oxygen transfer. Two phenomena govern the bubble size in a gas-liquid reactor or fermenter: the breaking of the bubbles and their coalescence. They make it possible, respectively, to reduce and to increase the bubble size, and thus to increase and to reduce the mass transfer. Thus, the inventors considered that if, by a particular means, the coalescence phenomenon were to be reduced, this would make it possible to increase the mass transfer and thus the maximum concentration of biomass achievable in a given fermenter, while at the same time maintaining the dissolved oxygen above the required minimum value.

There are many molecules which can partially block the coalescence of bubbles in aqueous medium, such as surfactants, for instance Sodium Dodecyl Sulfate (SDS) or Bovine Serum Albumin (BSA). These molecules nevertheless have the drawback of generating substantial foaming in these fermentation media, which is a real problem in the industrial implementation of the process, and they also have a negative impact in terms of cost of starting materials.

Finally, the inventors have observed that the fungus *Trichoderma reesei* produces numerous proteins during the growth step, and above all during the production step. Among these proteins, the family of molecules known as hydrophobins proved to be of particular interest. Specifically, these molecules have a considerable impact on the coalescence and thus the size of the bubbles, and their presence substantially increases the transfer performance. However, they have the drawback of being predominantly secreted during the production step, whereas the gas-liquid transfer is a substantial phenomenon above all in the growth step and not in the production step.

The present invention thus exploited this property of hydrophobins, by extracting them at the end of the production phase to reinject them into the growth phase. The hydrophobins produced in the production phase are, as it were, recycled into the growth phase. This solution has many advantages: the hydrophobins play their role of limiting coalescence in the growth phase, which ultimately makes it possible to reduce the costs associated with the stirring means (equipment cost and energy cost) and/or to have a higher concentration of fungi for a given reactor volume/type.

It is also pointed out that the invention does not give rise to any significant complication in the implementation of the enzyme production process, and does not oblige any specific genetic modifications on the microorganisms.

The invention proposes different variants/different embodiments for extracting the hydrophobins from the production medium, with various possible types of separation.

Preferably, the process according to the invention comprises after the enzyme production step (b) and before step (d) of reintroducing the hydrophobins, at least one step (c) of separating out the hydrophobins, notably in liquid phase, which is performed on the culture medium from the production step (b), notably by means of one or more successive filtrations of said culture medium.

According to a first variant, step (c) of separating out the hydrophobins is performed by direct separation of at least a portion of the hydrophobins in liquid phase from the culture medium of the production step (b). The hydrophobins are thus separated out directly (for example by filtration) from the fermentation culture medium, and the fungi (alternatively referred to as cell biomass in the present text) and the enzymes are left together for their subsequent combined use in a lignocellulosic biomass conversion process: specifically, in certain configurations, the enzymatic hydrolysis of the lignocellulosic biomass may be performed by placing in contact with a fermentation must starting with the mixture of fungi and enzymes that have been produced, without the need to separate the fungi from the enzymes.

According to a second variant, the process comprises, after the production step (b) and before step (d) of reintroducing the hydrophobins, a separation step (c) comprising a first substep (c1) of separation between, on the one hand, the fungi and, on the other hand, the rest of the culture medium, and then a second substep (c2) of separation of said rest of the culture medium between, on the one hand, the hydrophobins, notably in liquid phase, and, on the other hand, the enzymes. It is thus envisaged in this variant first to separate the fungi from the culture medium, for example by filtration, which makes it possible to recover a filtrate rich in enzymes and in hydrophobins, and then to separate the enzymes from the hydrophobins, which makes it possible to recover, if this separation is performed by filtration, a filtrate rich in hydrophobins (and poor in enzymes) which will be able to be used, totally or partly, in the growth step, whereas the enzymes thus isolated will be able to be used for the enzymatic hydrolysis of lignocellulosic biomass.

According to a preferred embodiment, step (c) of separating the hydrophobins (either from the rest of the culture medium or from the enzymes according to the two variants notably mentioned above) comprises at least one ultrafiltration of the hydrophobins from the liquid medium in which they are present, in order to isolate the hydrophobins in the filtrate in liquid phase. This ultrafiltration is preferably performed with a filtration membrane having a cut-off threshold of between 3 and 30 kDa, notably between 5 and 15 kDa. Specifically, a very advantageous characteristic in the context of the present invention concerning hydrophobins, and notably the molecule HFBII, is that they are much smaller than enzymes such as cellulases or hemicellulases, about 7 kDa as opposed to 30 to 100 kDa notably for cellulases, which makes the separation of these molecules by filtration/ultrafiltration entirely suitable, even though any other known separation technique may also be used: the membranes thus filter in the retentate all the components larger in size than the hydrophobins, which can then be isolated and collected in the filtrate in liquid phase.

Preferably, substep (c1) of separation between the fungi and the rest of the reaction medium according to the second variant is performed by filtration, notably with a filter press, even though any other known separation technique may also be used.

Preferably, the process according to the invention comprises, and preferably consists of, the steps a) of growth, b) of production, c) of separation, either in a single step or, in particular, consisting of the substep c1 and then the substep c2, and d) of reintroduction of the hydrophobins into step a).

Irrespective of the manner in which the hydrophobins are separated from the culture medium, preferably, the hydrophobins isolated after separation (c) and before reintroduction (d) into the culture medium of step (a) are in liquid phase, with optional intermediate storage, and optional intermediate dilution and/or concentration. Their handling and their introduction into the growth step (a) are thereby facilitated, all the more so when the liquid phase in question is an aqueous phase obtained from filtration of the culture medium from the production step (b): this aqueous phase is thus a top-up or even a replacement for the aqueous phase of the culture medium from step (a), which amounts to recycling the water from the production medium to the growth medium.

Advantageously, the hydrophobins produced in the production step (b) that are reintroduced into the growth step (a) are predominantly, notably essentially, type II hydrophobins. Among the hydrophobins, the molecule HFBII is in fact a predominant molecule, having a strong impact on the bubble size.

The growth step (a) and/or the production step (b) may be performed in batch, fed-batch or continuous mode, or in several of these modes successively.

In step (d), the hydrophobins may be reintroduced into the culture medium of the growth step (a) in various ways: continuously, in a single portion (at the start of or during the growth step (a)), or sequentially throughout all or part of the duration of said growth step (a). As mentioned above, intermediate storage may be envisaged, for example by providing a buffer tank.

Preferably, hydrophobins produced in the production step (b) are reintroduced into the growth step (a) in the form of a filtrate in aqueous phase obtained from the culture medium of step (b), the water of the culture medium of the growth step (a) coming totally or partly from said filtrate.

Preferably, hydrophobins are reintroduced into the growth step (a) in solution in an aqueous medium at a concentration of between 10 and 400 mg/l, preferably between 50 and 200 mg/l. Thus, either, when they are extracted from the culture medium by filtration, they are already in this concentration range in the aqueous filtrate obtained and at a suitable concentration, or this filtrate may, before reintroduction into the growth medium, be diluted or concentrated, to reach this range or to reach a different concentration value within this range.

Preferably, during the first growth step (a), the concentration of carbon-based growth substrate is chosen between 15 and 100 g/l, notably between 15 or 20 and 60 g/l.

Preferably, the second production step (b) is performed with a limiting stream of inductive carbon-based substrate, notably between 30 and 140 mg·g-1·h-1 (i.e. between 30 and 140 mg per gram of biomass and per hour), preferably between 35 and 45 mg·g-1·h-1, and preferably with an aqueous solution of carbon-based substrate(s) at a concentration of between 200 and 700 g/l. This solution of carbon-based substrate(s) comprises at least one inductive carbon-based substrate, which may be chosen from lactose, sophorose, cellulose, cellobiose, a cellulose marc or a mixture of at least two thereof.

Advantageously, the strain used is a strain of *Trichoderma reesei* or of *Trichoderma reesei* modified by selective mutation or genetic recombination. It may notably be the strain CL847, RutC30, MCG77 or MCG80 mentioned above. However, needless to say, and contrary to the teaching of the abovementioned patent application EP-1 204 738, the mutations envisaged in the context of the invention are not for the purpose, quite to the contrary, of preventing the formation of hydrophobins during the growth of said strain.

Optionally, the process according to the invention may comprise an intermediate step between step (a) and step (b), this intermediate step being a step of diluting the culture medium obtained from the growth step (a).

In addition, the growth step (a) and the production step (b) may be performed in the same bioreactor or in two different bioreactors, with transfer of the reaction medium from one reactor to the other. The first case is the simpler: with only one reactor, the need to transfer the reaction medium is avoided. The second case enables precise adaptation of the characteristics and equipment of each of the bioreactors as a function of the needs of each of the steps. Use may be made of different types of bioreactors, for example including bubble columns.

A subject of the invention is also the use of the enzymes obtained via the process described above for the enzymatic hydrolysis of terrestrial or marine cellulosic/hemicellulosic biomass.

A subject of the invention is also the production facility implementing the process described above, which may comprise a single bioreactor for the growth and production steps, or two different bioreactors and which is equipped with separation means, notably filtration means, capable of isolating the hydrophobins produced in the production phase, notably such as ultrafiltration means.

The hydrophobins may be reintroduced directly from one reactor to another, notably when two different reactors are used for each of the growth and production steps.

An intermediate container may be provided, in which the hydrophobins withdrawn in the production phase are stored, to reintroduce them subsequently into the growth phase (in the same reactor or a different reactor).

An intermediate solution may also be provided, partly with temporary storage of the hydrophobins withdrawn in the production phase for subsequent use, and partly with direct reintroduction into the growth phase in a reactor.

The invention will be described below in greater detail with the aid of non-limiting implementation examples.

DESCRIPTION OF THE EMBODIMENTS

Figure 1:
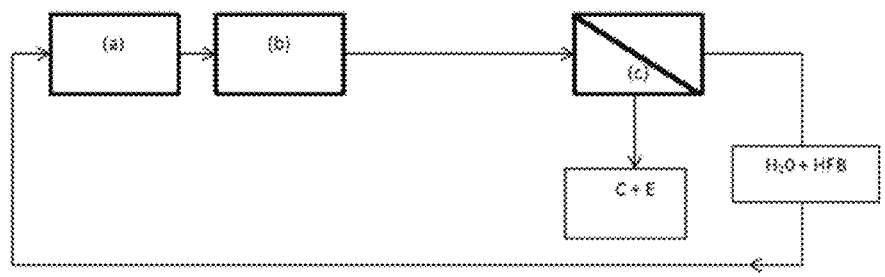
FIG. 1 is a block diagram of an enzyme production process according to a first variant of the invention.

FIG. 1 corresponds to the first variant of the enzyme production process according to the invention. The coalescence-limiting molecules are hydrophobins produced during the carbon-based substrate limitation phase. The process involves:
a step (a) of growing the fungi
and then a growth step (b)
according to the invention, a step (c) of separation by ultrafiltration is added, making it possible to obtain, on the one hand, a retentate F+E rich in fungi and in enzymes which they have produced, and, on the other hand, a filtrate containing water (the culture medium of steps (a) and (b) is aqueous) enriched in hydrophobins. This filtrate is then reinjected into the growth step (a). Before reinjection, it may be diluted or, more frequently, concentrated, and it may also be temporarily stored.

In this variant, the hydrophobins are thus filtered directly from the fermentation medium, and the fungi and enzymes are left together. This variant is particularly advantageous when the downstream process using the enzymes can exploit these enzymes without prior separation from the fungi: only one separation is necessary to perform the invention.

Figure 2:
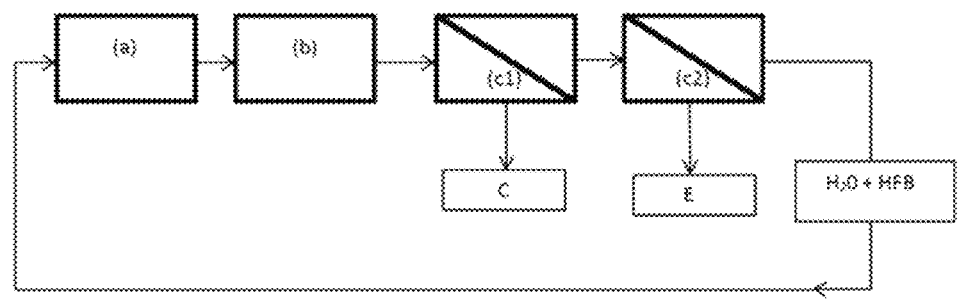
FIG. 2 is a block diagram of an enzyme production process according to a second variant of the invention.

FIG. 2 corresponds to a second variant of the process according to the invention. The growth step (a) and then the production step (b) are found. Two successive separations according to the invention are envisaged here: first a separation (c1), for example by filtration with a filter press, making it possible to separate, on the one hand, a retentate F rich in fungi, and, on the other hand, a filtrate enriched in enzymes and hydrophobins. Next, this filtrate undergoes a separation (c2) by ultrafiltration making it possible to recover, on the one hand, a retentate enriched in enzymes, and, on the other hand, a filtrate comprising water and enriched in hydrophobins, this filtrate then being reinjected, as in the preceding variant, into the growth step (a).

The enzymes have thus been separated here from the rest of the culture medium, which is advantageous when the downstream process uses these enzymes in pure form or to market them.

In these two variants notably, but for any other variant of the invention, there is a separation in the production step (b). It should be noted that this separation preferentially takes place at the end of step (b), and that this reinjection preferentially takes place at the start of step (a). However, it is also possible to perform the separation via methods other than filtration, and it is also possible for the separation to be performed throughout step (b) or over only a portion of its duration. Similarly, the reinjection of the hydrophobins into step (a) may also take place gradually over all or part of the duration of step (a).

The hydrophobins are preferably reintroduced in aqueous liquid form (they are obtained directly in this form by performing the separations by filtration). After adjusting the concentration in the liquid phase, this liquid phase may even entirely replace the water used for the culture medium of the growth step (a).

Implementation Examples

Two comparative growths of *Trichoderma reesei* in a 30 L bioreactor were performed: The first is performed with a conventional culture medium, and the second is performed by replacing the water with a hydrophobin-rich filtrate obtained from a previous production. This filtrate was obtained by filtering the culture medium by ultrafiltration with membranes having a 10 kDa cut-off threshold; it was then concentrated.

Rheological measurements and kLa measurements are performed in both cases. In the first case, it is seen that the viscosity greatly affects the oxygen transfer (as demonstrated in the abovementioned 2012 article by Gabelle J.-C.). In the second case, despite the high viscosity, supplying hydrophobins has a positive impact on the kLa of the medium, which becomes equivalent to, or even higher than, that of water, obtained under the same stirring and aeration conditions.

The rheology measurement is used according to the method described in the following article:
Nicolas Hardy, Frederic Augier, Alvin W. Nienow, Catherine Béal, Fadhel Ben Chaabane. Scale-up agitation criteria for *Trichoderma reesei* fermentation: Chemical Engineering Science, Elsevier, 2017, 172, pages 158-168(10.1016/j.ces.2017.06.034).

Calculation of the kLa is performed via the known gas balance method described in the abovementioned article: Gabelle J. C., Jourdier E., Licht R. B., Ben Chaabane F., Henaut I., Morchain J., and Augier F. (2012) Impact of rheology on the mass transfer coefficient during the growth phase of *Trichoderma reesei* in stirred bioreactors. Chemical Engineering Science 75, 408-417. The reactor used is a 30 L bioreactor. Its configuration is described in the same article.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 19/12.856, filed Nov. 18, 2019, are incorporated by reference herein.

Example 1 (Comparative Example—Invention Preliminary)

The growth of *Trichoderma reesei* is performed in the abovementioned mechanically stirred 30 L fermenter with a working volume of 20 L. The mineral medium has the following composition: KOH 1.66 g/L, 85% $H_3PO_4$ 2 mL/L, $(NH_4)_2SO_4$ 2.8 g/L, $MgSO_4.7H_2O$ 0.6 g/L, $CaCl_2$) 0.6 g/L, $MnSO_4$ 3.2 mg/L, $ZnSO_4.7H_2O$ 2.8 mg/L, $CoCl_2$ 104.0 mg/L, $FeSO_4.7H_2O$ 10 mg/L, Corn Steep 1.2 g/L, antifoam 0.5 mL/L (which will be at least partly consumed by the microorganism). Mains water is used to dilute the various components of the medium and to fill the reactor so as to obtain a final volume of 20 L.

The fermenter containing the mineral medium is sterilized at 120° C. for 20 minutes, the carbon-based glucose source is sterilized separately at 120° C. for 20 minutes and then added under sterile conditions to the bioreactor so as to obtain a final concentration of 50 g/L. The fermenter is seeded with a liquid preculture of 1 L of the strain of *Trichoderma reesei* CL847. The mineral medium of the preculture is identical to that of the fermenter, except for the addition of potassium phthalate at 5 g·L$^{-1}$ to buffer the pH of the medium. The growth of the fungus in preculture is performed using glucose as carbon-based substrate, at a concentration of 30 g·L$^{-1}$. The growth of the inoculum lasts 2 to 3 days, and is performed at 28° C. in a shaking incubator. Transfer to the fermenter is performed when the residual glucose concentration is less than 15 g/L.

The growth step is performed for 50 hours in the stirred 30 L bioreactor at a temperature of 27° C. and a pH of 4.8 (adjusted with 5.5 M aqueous ammonia). The aeration is 0.5 vvm (volume/volume/minute) and the concentration percentage of dissolved oxygen relative to saturation in the liquid medium is adjusted to 40%. The fermenter is equipped with a stirrer containing two impellers with inclined straight paddles, rotating at a speed of 1200 rpm.

Samples are taken regularly to monitor the rheology of the medium and the concentration of cellular biomass. Since there are no insoluble components in the culture medium, the dry weight, determined by filtration and drying to constant weight, represents the mass of fungi, also known as the cellular biomass. An analyser at the bioreactor outlet makes it possible to monitor the $O_2$ and $CO_2$ composition of the gas.

The gas balances make it possible to continuously calculate the rate of $O_2$ consumption, $rO_2$ and the kLa:

This gives, at the pseudo-stationary state $$rO_2 = Q\text{in}*\% \ O_2\text{in} - Q\text{out}*\% \ O_2\text{out}$$

$$rCO_2 = Q\text{out}*\% \ CO_2\text{out} - Q\text{in}*\% \ CO_2\text{in}$$

with:
Qin: air flow rate at the inlet in mol/h
Qout: air flow rate at the outlet in mol/h
% $O_2$in: mol % of $O_2$ at the inlet
% $O_2$out: mol % of $O_2$ at the outlet
% $CO_2$in: mol % of $CO_2$ at the inlet
% $CO_2$out: mol % of $CO_2$ at the outlet The $rO_2$ is used to calculate the culture kLa by means of the combination of the two $O_2$ material balances on the liquid phase and the gas phase at the pseudo-stationary state:

$$kLa(t) = rO_2/(O_2^* - O_{2L})$$

with:
$O_2^*$: concentration of $O_2$ at saturation
$O_{2L}$: concentration of oxygen in the liquid According to Henrys law, the maximum concentration of a gas in solution, at equilibrium with an atmosphere containing this gas, is proportional to the partial pressure of this gas at this point.

This thus gives, for the case of $O_2$:

$$O_2^* (\text{mol/m}^3) = 1.25 pO \text{ (bar)}$$

with:
pO: partial pressure of $O_2$

It should be noted that the partial pressure of $O_2$ is equal to the product of the mole fraction of $O_2$ in the gas and of the pressure. The $O_2^*$ in an industrial fermenter is thus maximal at the bottom of the reactor (maximum pressure and percentage of $O_2$ at the inlet of 21%) and minimal at the top (headspace pressure and percentage of $O_2$ in the gas at the outlet). It is calculated at each moment in the experiment, since the $O_2$ composition of the exiting gas decreases due to the consumption of $O_2$ by the microorganism. In the case of a laboratory reactor, the pressure difference between the top and the bottom of the reactor is negligible.

The oxygen concentration in the liquid is calculated by means of the $pO_2$ probe measurement, which gives a percentage of $O_2$ relative to saturation.

Thus, during the growth of the fungus, it was possible to measure at different moments the concentration of cellular biomass (X), the viscosity (pa) of the fermentation medium at a shear of 10 s$^{-1}$, and a coefficient of gas-liquid transfer kLa in h$^{-1}$.

The kLa measurements are compared with a measurement taken in water, at the same air flow rate and the same stirring speed. Table 1 below presents the results for the transfer coefficients obtained during the fermentation according to the prior art.

TABLE 1

|  |  | kLa (h$^{-1}$) | kLa water (h$^{-1}$) |
|---|---|---|---|
| 2.5 | 0.03 | 180 | 217 |
| 3.8 | 0.055 | 150 | 217 |
| 9.2 | 0.21 | 82 | 217 |
| 16 | 0.48 | 45 | 217 |

The production phase was then performed at pH 4 at 25° C., with a lactose concentration of 220 g/L, corresponding to a specific fed-batch lactose flow rate of 45 mg per gram of biomass and per hour.

Example 2 (according to the invention) An experiment is performed under the same conditions, but replacing the water with a solution obtained from a previous cellulase production experiment on which a concentration of 100 mg/L of HFBII hydrophobins (only the HFBIIs were assayed, it is possible that the hydrophobins used also comprise other types of hydrophobins, in minor amount) was determined by HPLC (high-performance liquid chromatography) with a Wide Pore C5 column (150×2.1 mm; 5 μm) and UV detection. Filtration was performed at the end of this experiment to separate the fungus from the cellulases, and ultrafiltration with membranes having a porosity of 10 kDa (the recommended membranes are UFX 10 pHt membranes sold by the company Alfa Laval. The supplier's information should be adhered to for their use (pressure, temperature, etc. conditions). For the product, it is preferable not to exceed 30° C. during this ultrafiltration, 20 to 25° C. being a preferred temperature range. After ultrafiltration, the permeates contain the hydrophobins. Analysis of the mean permeate sample makes it possible to assay the sample. The flow rates obtained are 20 l/h/m$^2$ of membrane. Ultrafiltration makes it possible to concentrate the cellulases and to recover in the filtrate a medium containing hydrophobins. The hydrophobins concentration was then measured again by HPLC and is close to 100 mg/L. It is this solution which was used as dilution water in the 30 L bioreactor. It should be noted that additional water was added, thus diluting the hydrophobin concentration at the start (time T0) of the experiment by 25%. The operating conditions are the same as for Example 1.

The production phase is also conducted, after the growth phase, under the same operating conditions as for Example 1.

The viscosity and the transfer coefficient are measured during the growth of the fungus. The results obtained are presented in Table 2, which indicates the concentration of cellular biomass (X), the viscosity of the fermentation medium at a shear of 10 s$^{-1}$ (μa), and a coefficient of gas-liquid transfer kLa in h$^{-1}$ as in the preceding Table 1.

TABLE 2

|    | kLa (h⁻¹) |       | kLa water (h⁻¹) |
|----|-----------|-------|-----------------|
| 2  | 0.021     | 480   | 217             |
| 4  | 0.06      | 370   | 217             |
| 10 | 0.24      | 185   | 217             |
| 15 | 0.44      | 120   | 217             |

Figure 3:
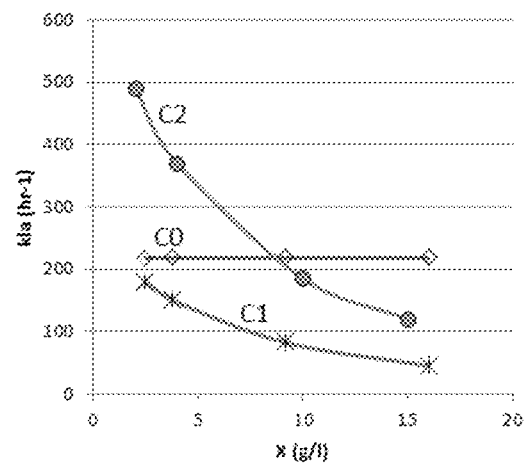
FIG. 3 is a graph representing, on the x-axis, the concentration of fungi (cellular biomass) in g/l, and, on the y-axis, the corresponding kLa in h$^{-1}$ for water (curve C0), and for Example 1 and Example 2 described below (curves C1 and C2, respectively).

A comparison of the performance obtained according to the two Examples 1 and 2 is shown on the graph of FIG. 3: It is noted that the transfer coefficients kLa obtained according to the invention (curve C1 for Comparative Example 1, curve C2 for Example 2 according to the invention) are at least two times higher than according to the prior art. Depending on the biomass concentration, the transfer coefficient is sometimes lower and sometimes higher than that measured in water (curve CO) under the same aeration and stirring conditions.

These examples show that the oxygen transfer is greatly facilitated by the invention. This advantage may be exploited in various ways, and notably:
- to lower the stirring speed in the bioreactor, to reach the target transfer coefficient while consuming less energy,
- to lower the air flow rate in the bioreactor, for the same reasons,
- to perform culturing with more cellular biomass, while at the same time remaining above a minimum target concentration of dissolved oxygen, which makes it possible to increase the productivity of the bioreactors (also known as fermenters).

It was also checked that the enzyme production performance of the two examples, evaluated at the end of the production phase, are the same or virtually the same for the two examples:

these advantages are thus not obtained at the expense of the performance or the production yield of the process.

As the transfer coefficient kLa is proportional to the power dissipated per unit volume (P/V, expressed in W/m³), within a power range per unit volume P/V of between 0.4 and 0.5 kW/m³ (according to the abovementioned 2012 article by Gabelle et al.), increasing the kLa by a factor of at least 2 makes it possible to save between 75% and 85% of the power dissipated per unit volume, which is an enormous saving at the industrial scale.

It should moreover be noted that while Examples 1 and 2 use specific carbon sources for the growth and for the production, the invention naturally applies with other carbon sources, such as soluble sugars, for instance lactose, glucose or xylose. The carbon-based growth substrate may be chosen from lactose, glucose, xylose, residues obtained after ethanolic fermentation of monomer sugars from the enzymatic hydrolysates of cellulose-based biomass, and/or a crude extract of water-soluble pentoses obtained from the pretreatment of a cellulose-based biomass. The inductive carbon-based substrate is preferably chosen from lactose, cellobiose, sophorose, residues obtained after ethanolic fermentation of monomer sugars from the enzymatic hydrolysates of cellulose-based biomass, and/or a crude extract of water-soluble pentoses obtained from the pretreatment of a cellulose-based biomass. This type of residue/extract may thus also be used as a source of total carbon, i.e. both for the growth of the microorganism and for the induction of the expression system. This carbon source may be used more particularly by genetically enhanced strains and notably recombinant strains.

Similarly, the invention also applies under operating conditions different from those expressly envisaged in the examples. Thus, the pH and the temperature, for the growth step and the production step, may be as follows:
pH between 3.5 and 4.4;
temperature between 20 and 35° C.

The vvm (degree of aeration expressed as volume of air per volume of reaction medium and per minute) applied during the process is between 0.3 and 1.5 min⁻¹ and the rpm (stirring speed) must make it possible to regulate the concentration percentage of dissolved oxygen relative to saturation in the liquid medium to between 20% and 60% of $O_2$. An aeration of 0.3 to 0.5 min⁻¹ and stirring which makes it possible to regulate the concentration percentage of dissolved oxygen to between 30% and 40% of $O_2$ are preferably chosen.

Depending on its nature, the carbon-based substrate chosen for the production of the biomass is introduced into the fermenter before sterilization, or is sterilized separately and introduced into the fermenter after sterilization. The concentration of carbon-based substrate is between 200 and 700 g/L depending on the degree of solubility of the carbon-based substrates used (notably as regards the inductive substrate which forms part of these carbon-based substrates).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing cellulolytic and/or hemicellulolytic enzymes with a strain of *Trichoderma reesei* or of *Trichoderma reesei* modified by selective mutation or genetic recombination, said process comprising:
a step (a) of growing the fungi in an aqueous culture medium, in the presence of at least one carbon-based growth substrate in a stirred and aerated bioreactor,
a step (b) of producing enzymes from the aqueous culture medium obtained in the first step (a), in the presence of at least one inductive carbon-based substrate and also producing hydrophobins, wherein step (b) results in the aqueous culture medium comprising enzymes, fungi and hydrophobins;
at least one separation step (c) performed on the aqueous culture medium from the production step (b) comprising separating out the hydrophobins in a liquid phase by filtration, and
a step (d), wherein the hydrophobins produced in step (b) and separated in step (c) are reintroduced into the growth step (a), and
wherein the process during step a), has a volumetric oxygen transfer coefficient $K_La$ of 185 to 480.

2. Process according to claim 1, wherein step (c) is performed by direct separation of at least a portion of the hydrophobins in liquid phase from the culture medium of the production step (b), wherein direct separation comprises a single step where hydrophobins are separated from the fungi and enzymes of the aqueous culture medium.

3. Process according to claim 1, wherein the, a separation step (c) comprises a first substep (C1) of separation between the fungi and the rest of the culture medium, and then a second substep (c2) of separation of the remainder of culture medium between the hydrophobins in liquid phase, and the enzymes.

4. Process according to claim 1, wherein the separation step (c) comprises at least one ultrafiltration of the hydrophobins from the liquid medium in which they are present so as to isolate the hydrophobins in the filtrate in the liquid phase.

5. Process according to claim 3, wherein the substep (c1) of separation between the fungi and the rest of the reaction medium is performed by filtration.

6. Process according to claim 1, wherein the hydrophobins isolated after separation step (c) are stored and diluted or concentrated before reintroduction step (d).

7. Process according to claim 1, wherein the hydrophobins produced in the production step (b) that are reintroduced into the growth step (a) are at least 50% type II hydrophobins.

8. Process according to claim 1, wherein the growth step (a) is performed in batch mode, fed-batch mode, continuous mode, or in several of these modes successively.

9. Process according to claim 1, wherein in step (d), the hydrophobins are reintroduced into the culture medium of the growth step (a) continuously, throughout the duration of said growth step (a).

10. Process according to claim 1, wherein the hydrophobins produced in the production step (b) are reintroduced into the growth step (a) in the form of a filtrate in aqueous phase obtained from the culture medium of step (b), the water of the culture medium of the production step (a) coming totally or partly from said filtrate.

11. Process according to claim 1, wherein the hydrophobins are reintroduced into the growth step (a) in solution in an aqueous medium at a concentration of between 10 and 400 mg/l.

12. Process according to claim 1, wherein during the growth step (a), the concentration of carbon-based growth substrate is between 15 and 100 g/l, and wherein the production step (b) is performed with a limiting stream of inductive carbon-based substrate, of between 30 and 140 $mg \cdot g^{-1} \cdot h^{-1}$.

13. Process according to claim 1, wherein the production step (b) is performed in batch mode, fed-batch mode, continuous mode, or in several of these modes successively.

14. The process of claim 1 wherein the growth step (a) is performed in batch mode and the production step (b) is performed in fed-batch mode.

15. A process for producing cellulolytic and/or hemicellulolytic enzymes with a strain of *Trichoderma reesei* or of *Trichoderma reesei* modified by selective mutation or genetic recombination, said process comprising:
   a step (a) of growing the fungi in an aqueous culture medium, in the presence of at least one carbon-based growth substrate in a stirred and aerated bioreactor,
   a step (b) of producing enzymes from the aqueous culture medium obtained in the first step (a), in the presence of at least one inductive carbon-based substrate and also producing hydrophobins, wherein step (b) results in the aqueous culture medium comprising enzymes, fungi and hydrophobins;
   at least one separation step (c) performed on the aqueous culture medium from the production step (b) comprising separating out the hydrophobins in a liquid phase by filtration, and
   a step (d), wherein at least a portion of the hydrophobins produced in step (b) and separated in step (c) are reintroduced into the growth step (a), and
   wherein the reintroduced hydrophobin concentration is in the range of 10-400 mg/l and wherein the process during step (a), has a volumetric oxygen transfer coefficient $K_La$ of 185 to 480.

16. The process of claim 15, wherein the reintroduced hydrophobin concentration is in the range of 50-200 mg/l.

* * * * *